United States Patent [19]
Watanabe et al.

[11] Patent Number: 5,648,332
[45] Date of Patent: Jul. 15, 1997

[54] METHOD OF TREATING DIABETES MELLITUS USING VARIABLE α DOMAIN OF T-CELL RECEPTOR

[75] Inventors: Hiroshi Watanabe, Hatoyama-machi; Nobuyuki Yamagata, Kawagoe; Masaru Taniguchi, Chiba, all of Japan

[73] Assignee: Hoechst Japan Limited, Tokyo, Japan

[21] Appl. No.: 318,881

[22] PCT Filed: Feb. 22, 1994

[86] PCT No.: PCT/IB94/00029

§ 371 Date: Oct. 20, 1994

§ 102(e) Date: Oct. 20, 1994

[87] PCT Pub. No.: WO94/19470

PCT Pub. Date: Sep. 1, 1994

[30] Foreign Application Priority Data

Jul. 20, 1993 [JP] Japan ................................. 5-179062
Feb. 22, 1994 [JP] Japan ................................. 5-031501

[51] Int. Cl.$^6$ ................................................ A61K 38/17
[52] U.S. Cl. ........................................................ 514/12
[58] Field of Search ............................ 514/12; 435/69.7

[56] References Cited

FOREIGN PATENT DOCUMENTS 9110438 7/1991 WIPO.

OTHER PUBLICATIONS

Davies et al. (1991). New England Journal of Medicine 325, 238–244.
Yamamura et al. (1994). International Immunology 6, 947–954.
Ito et al. (1991). International Immunology 3, 991–995.
Vandenbark et al. (1989). Nature 341, 541–544.
Koseki et al. (1992). Int'l. Archives of Allergy and Immunology 99, 416–418.

*Primary Examiner*—Stephen Walsh
*Assistant Examiner*—Karen E. Brown
*Attorney, Agent, or Firm*—Finnegan, Henderson, Farabow, Garrett & Dunner, L.L.P.

[57] ABSTRACT

A soluble T-cell receptor α-chain produced by suppressor T-cell. The said soluble T-cell receptor α-chain is useful as a prophylactic and therapeutic agent for autoimmune diseases generated to a wide variety of autoantigens irrespective of specificity to the said suppressor T-cell.

2 Claims, 3 Drawing Sheets

METHOD OF TREATING DIABETES MELLITUS USING VARIABLE α DOMAIN OF T-CELL RECEPTOR

BACKGROUND OF THE INVENTION

1. Field of the Invention

This invention relates to a prophylactic and therapeutic agent for autoimmune diseases. More particularly, it is concerned with a prophylactic and therapeutic agent for autoimmune diseases generated to a wide variety of autoantigens which comprises as an active ingredient of a soluble T-cell receptor α-chain produced by the said suppressor T-cell. 2. Description of the Prior Art Autoimmune diseases are meant to be a generic term for the immune diseases which would cause various disturbances by forming autoantibodies and cytotoxic T-cells to the antigen derived from autologous tissues. The autoimmune diseases may include non-organ specific diseases such as systemic lupus erythematosus, chronic rheumatoid arthritis, systemic sclerosis, dermatomyositis/multiple myositis, Sjogren's syndrome and others; organ specific diseases such as diabetes, Hashimoto's thyroiditis, Graves' disease, multiple sclerosis, idiopathic Addison's disease, myasthenia gravis, pernicious anemia, and others; as well as mixed diseases such as primary biliary cirrhosis, chronic active hepatitis and others, and the total number of those patients suffering from such diseases including latent patients has been enormous.

The therapy hitherto practically applied for the treatment of such autoimmune diseases may include administration of such therapeutic agents as corticosteroids, cyclosporin A, cyclophosphamide, azathiopurine, methotrexate and the like, expecting their immunosuppressive activity; or X-ray irradiation, thymectomy and others; or administration of interferon, γ-globulin, antibody to lymphoid cell surface marker, gold preparations, D-penicillamine and the like, expecting their immunoregulating activity.

Many of such immunosuppressants could damage the DNA or RNA in various cells including immunocompetent cells and, accordingly, there would be developed severe side-effects if one may use them in an erroneous manner. Moreover, administration to pregnant women would cause birth of malformed babies and it has been also pointed out that there may be strengthened a risk of opportunistic infection because of widespread immunosuppression induced. On the other hand, a detailed mechanism of action in an immune regulator has not yet been known so that it would be difficult to predict a therapeutic effect exactly. And further, it has been pointed out that there would be a high risk of side-effects because of a wide variety of cell groups to be influenced.

As discussed above, there have been found many unsatisfactory points in the existing, therapies against autoimmune diseases. Also, there have been found many unsolved points in the mechanism of onset of autoimmune diseases. It has been strong grounds to hinder development of the therapeutic agent capable of acting specifically on abnormal portions only in the immune system, inducing autoimmune diseases.

DESCRIPTION OF THE INVENTION

Figure 1:
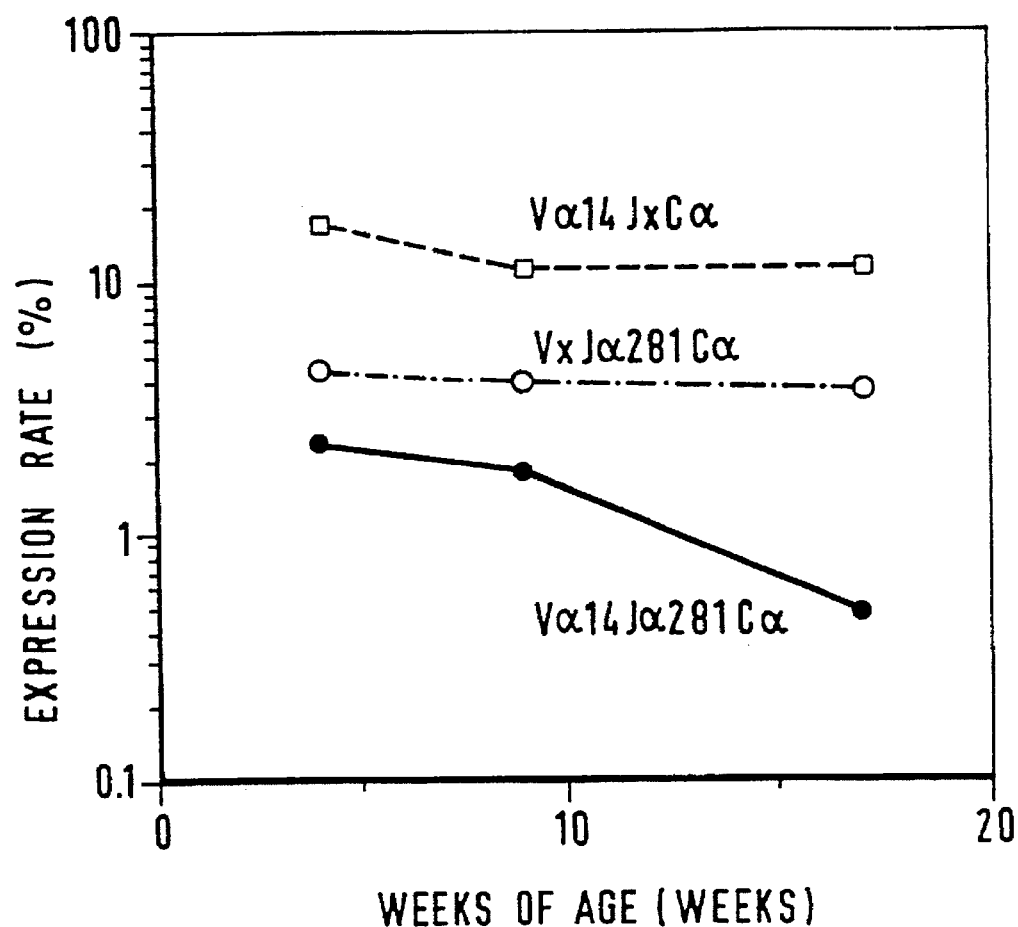
FIG. 1 shows the results wherein the expression levels of the mRNA encoding the T-cell receptor αchain, Vα14Jα281 in spleen lymphocytes of NOD mice were determined every week of age. In this Figure, the closed circles show changes in the mRNA corresponding to the present Vα14Jα281Cα, while the open circles and open squares show changes in the mRNA corresponding to VxJα281Cα and Vα14JxCα employed as the control groups, respectively.

It is hopefully believed to establish a complete therapy with less side-effects, depending upon abnormal portions in the immune system to be targeted, if there could be developed a therapeutic agent capable of exerting a specific effect on immune diseases. Thus, with the purpose of setting a specific therapy, the present inventors have attempted to establish a therapeutic method for autoimmune diseases by producing a soluble T-cell receptor (hereinafter abbreviated as TCR) α-chain as T-cell derived suppressor factor (hereinafter abbreviated as TsF) which can locally prevent an anomalous acceleration of the immune system.

The suppressor T-cell (hereinafter abbreviated as Ts) as used herein does mean to be a series of those cell groups capable of showing an immunosuppressive activity, which show an antigen-specific action in the early stage of inducing immunosuppression and an antigen non-specific action in the final stage of exerting suppressive activity. Namely, the suppressor T-cell is a subgroup of the T-cells which have a quite reverse action to that of the helper T-cell (hereinafter abbreviated as Th) which could antigen-specifically enhance immune reaction.

In human beings and other animals suffering from autoimmune diseases, there have been reported several qualitative or quantitative abnormalities of Ts [Mcintosh and Drachman, Science, 232, 401 (1986); Isenberg et al., Br. Med. Bull., 10, 262 (1984).] Where the Ts function abnormality is induced, production of TsF would be reduced, while the Th activity could relatively be enhanced. Thus, it is believed that cytotoxic T-cell-inducing T-cell and then auto-toxic T-cell could be induced and activated. Autoantibody-producing B-cell could similarly be activated. Accordingly, where tissue cells or biologically active factors are attacked by the immune system in autoimmune diseases, it may be expected that the portions to which abnormality of such an immune disease could be attributed can be repaired by administering to the patient suffering therefrom the TsF produced by the specific Ts to the targeted antigen, which may result in complete recovery of the disease.

The present KLH (keyhole limpet hemocyanin)-specific Ts, which can be derived from the mice immunized as an antigen with the KLH was isolated as the Ts hybridoma by Taniguchi et al., Nature, 278, 555 (1979). Selection of the Ts hybridoma was performed by using as a standard the prevention of the KLH-specific antibody. Taniguchi et al. have confirmed a production of the soluble TsF by the Ts hybrydoma. The TsF was absorbed by the immunoadsorbent coated with the KLH and could specifically prevent in vitro the antibody production to the KLH. It was suggested by Imai et al. [Proc. Natl. Acad. Sci. USA, 83, 8708 (1986)] that, as a result of the gene analysis of the Ts hybrydoma cell, the TCR to the antigen expressed by the KLH-specific Ts was the TCR α-chain and that the TCR α-chain plays an important role in the development of the suppressive function.

Moreover, Koseki et al. performed cloning of the cDNA and genomic DNA for the α-chain receptor from the Ts hybrydoma to determine the base sequence [Int. Immunol., 1, 41 (1989)]. Consequently, they found an entirely new gene family for the variable region of the α-chain (hereinafter abbreviated as Vα) and named it "Vα14", which is different from any Vα families already known in the art. More than 90% of Vα14 was bound by gene rearrangement with Jα281, one sort of the joining region of α-chain (hereinafter abbreviated as Jα).

Recent research results have elucidated the character of the TsF derived from a suppressor T-cell [Batchelor et al., Immunol. Today, 10, 37 (1989)]. More specifically, the function of TsF to bind antigen is borne by the TCR α-chain, which is then liberated from Ts to form TsF. Accordingly, the soluble α-chain is to be applied to the therapy of autoimmune diseases as the TsF specifically inducing immunosuppression. As the structure of the TCR α-chain of Ts may be considered to be different from the α-chain of Th and cytotoxic T-cells [Imai et al., Proc. Natle. Acad. Sci. USA, 83, 8708 (1986)], it is believed that the object of the invention could not be accomplished even by using the α-chain derived from Th or cytotoxic T-cells. Then, the most reasonable and possible approach to develop the therapeutic agent is to restrict to the α-chain produced by Ts.

However, it could be envisaged upon prior reports that the antigen specific TsF may be applied to suppression of production of the antibody to the said foreign antigen, but it could not be expected at all to apply for suppression of autoimmune responses, namely, for therapy of autoimmune diseases.

On the other hand, Fairchild et al. found that the dinitrophenol (hereinafter abbreviated as DNP) antigen specific CD (cluster of differentiation) 8 positive Ts [Fairchild et al., J. Immunol., 141, 3342 (1988); Fairchild et al., ibid, 145, 2001 (1990)] produced a soluble dimer TsF consisting of α-chain and β-chain. And further, it is also reported that Lider et al. made usage analysis of TCR of the dimer consisting of α-chain and β-chain which was very frequently found in encephalitogenic T-cells of experimental allergic encephalomyelitis, (hereinafter abbreviated as EAE)[Lider et al., Science, 239, 181 (1988)] and succeeded in vaccination using synthetic peptides of Vβ8 region [Vandenbark et al., Nature, 341, 541 (1989)] or β-chain VDJ region and J region [Howell et al., Science, 246, 668 (1989)] in the presence of an adjuvant. However, confirmation tests conducted under the same conditions frequently revealed reverse results (Desquenne-Clark et al., Proc. Natl. Acad. Sci. USA, 88, 7219 (1991)]. Namely, the experiments by Desquenne-Clark et al. have revealed that vaccination to rats using the above-mentioned synthetic peptide chain derived from encephalitogenic T-cells could not suppress EAE, but rather EAE symptoms would frequently grow worse.

Moreover, the TCR β-chain participates in the restriction of the major histocompatibility complex (hereinafter abbreviated as MHC) and hence not only the β-chain alone but the dimer of the α-chain and the β-chain may not be regarded adequate for use as a therapeutic agent. The reason therefore is that individual human beings have different MHCs and it is not practical, though not impossible, to prepare a therapeutic agent adequate for individual patients. As the present TCR α-chain could recognize the antigen only, a therapeutic effect can be expected without receiving any restriction of the MHC by administering the α-chain to patients. Accordingly, one therapeutic agent prepared according to this invention may be applicable to all patients suffering from a certain auto-immune disease without considering any difference in an individual MHC.

Summarizing up the above consideration, the TCR α-chain as TsF produced and released from Ts can exert an immunosuppressive activity and then it can be expected to exert an effective activity as the therapeutic agent for autoimmune diseases. The antigen-specific immunosuppressive activity is believed to be followed finally by antigen non-specific immunosuppression at lesion sites via cytokines such as TGF (transforming growth factor)-β or IL (interleukin)-10 and the like. The concept utilized in this invention may be applicable to development of therapeutic agents for all autoimmune diseases.

Then, in order to confirm the effectiveness of the above concept through experiments, the present inventors have studied a therapeutic effect on insulin-dependent diabetes mellitus (hereinafter abbreviated as IDDM). They have produced a soluble form of the Vα14Jα281, which is a functional site of the TCR, by a recombinant protein method, after which it was administered in the absence of adjuvant to NOD (nonobese diabetic) mice with abiogenetic IDDM. More specifically, mice were immunized with an exogenous antigen KLH, the KLH-specific Ts hybrydoma was established in vitro and the cDNA encoding TCR was cloned from the Ts hybridoma to obtain the cDNA of Vα14Jα281 used in this invention. Thereafter, the Vα14Jα281 cDNA was inserted into an expression plasmid containing mouse Cγ3 to perform expression in myeloma cells as a chimeric protein. By this chimeric formation, the Vα14Jα281 has become structurally stable and could be obtained as a soluble protein from the supernatant of the transformed myeloma cell culture. The Cγ3 as derived from mice does not act as a carrier to hapten in experiments with mouse strains, therefore, the immune reaction against the Cγ3 of the chimeric protein was not induced.

The indirect animal tests using the monoclonal antibody to the Vα14 afforded the results suggesting that the TCR Vα14Jα281 might also participate in the antigen-nonspecific immunosuppression reaction in an in vivo system. Also, it could result in a strong suggestion of the Vα14Jα281 participating in the antigen-nonspecific immune suppression that the expression of the mRNA encoding the Vα14Jα281 was suppressed in NOD mice as the time of onset of diabetes mellitus was getting close. As discussed above, one has expected a therapeutic effect of the soluble Vα14Jα281 on IDDM and a remarkable suppressive effect has been confirmed as a result of animal tests using IDDM model mice.

Vα14Jα281 is originally the TCR functional site of the KLH-specific Ts. Even if there is a possibility of high homology of the KLH with various autoantigens particularly being present in the pancreas and even if the immunosuppressive system may be antigen-specifically induced as discussed above, the final stage-generation of the antigen-nonspecific suppression to the autoreactive effector cell may be given in order to explain such an antigen-nonspecific immunosuppressive therapeutic effect in IDDM.

In any case, due to the above-mentioned antigen-nonspecific immunosuppressive effect of the Vα14Jα281, the soluble TCR can be expected to exert a wide therapeutic effect on not only IDDM but also other all autoimmune diseases.

The TCR Vα14 gene has been well kept in wild mouse strains [Koseki et al., Proc. Natl. Acd. Sci. USA, 87, 5248 (1990)]. Homology between the amino acid sequence of TCR Vα14 of mice and the amino acid sequence of the human counterpart TCR Vα family is as high as 76%, whereas homology of other members in about 100 of the Vα family, so far as it is known, is 70% or less. In view of such a high homology, the said human TCR Vα family is also believed to achieve a similar immunosuppressive function. Moreover, out of numerous Vα families, the mouse Vα14 having a specific function of immunosuppression is believed to be useful as a therapeutic agent to various human autoimmune diseases.

Participation in immunosuppression by the present Vα14Jα281 receptor and therapeutic effect on IDDM using NOD mice will be illustrated in detail by way of the following Examples.

EXAMPLE 1

Restriction of expression of TCR Vα14Jα281 mRNA in autoimmune disease mice

Expression of the mRNA encoding Vα14Jα281 in spleen lymphocytes of NOD mice was quantitatively assayed using RNase protection assay [Koseki et al., Proc. Natl. Acad. Sci, USA, 87, 5248 (1990)]. For this purpose, the cDNA encoding Vα14Jα281Cα coupling Vα14Jα281 with constant region of α-chain (hereinafter abbreviated as Cα) of TCR α-chain was integrated into the commercially available pCEM plasmid (available from Promega Biotec) to synthesize the Vα14Jα281Cα riboprobe labeled with an isotope using Sp6 promoter. The RNA extracted from lymphocytes and the probe was hybridized. The unhybridized portion was digested with single stranded specific RNase. The product was fractionated by agarose gel electrophoresis. The concentration of the band to be hybridized with Cα only was defined as 100% and the concentration of the corresponding Vα14Jα281 band was compared and calculated in terms of percentage to determine the expression frequency of the mRNA encoding Vα14Jα281. Also, in control groups, there were determined the expression frequency of the mRNA encoding Vα14JxCα group consisting of J region having Vα14 except Jα281 and that of the mRNA encoding VxJα281Cα groups consisting of V region having Jα281 except Vα14, respectively.

It has been found that expression of Vα14Jα281 mRNA in NOD mice was beyond 2% before onset, whereas it was reduced with aging at the time of onset. On the other hand, changes with aging were not observed in the control group. (See, FIG. 1)

EXAMPLE 2

Preparation of soluble TCR Vα14Jα281

Figure 2:
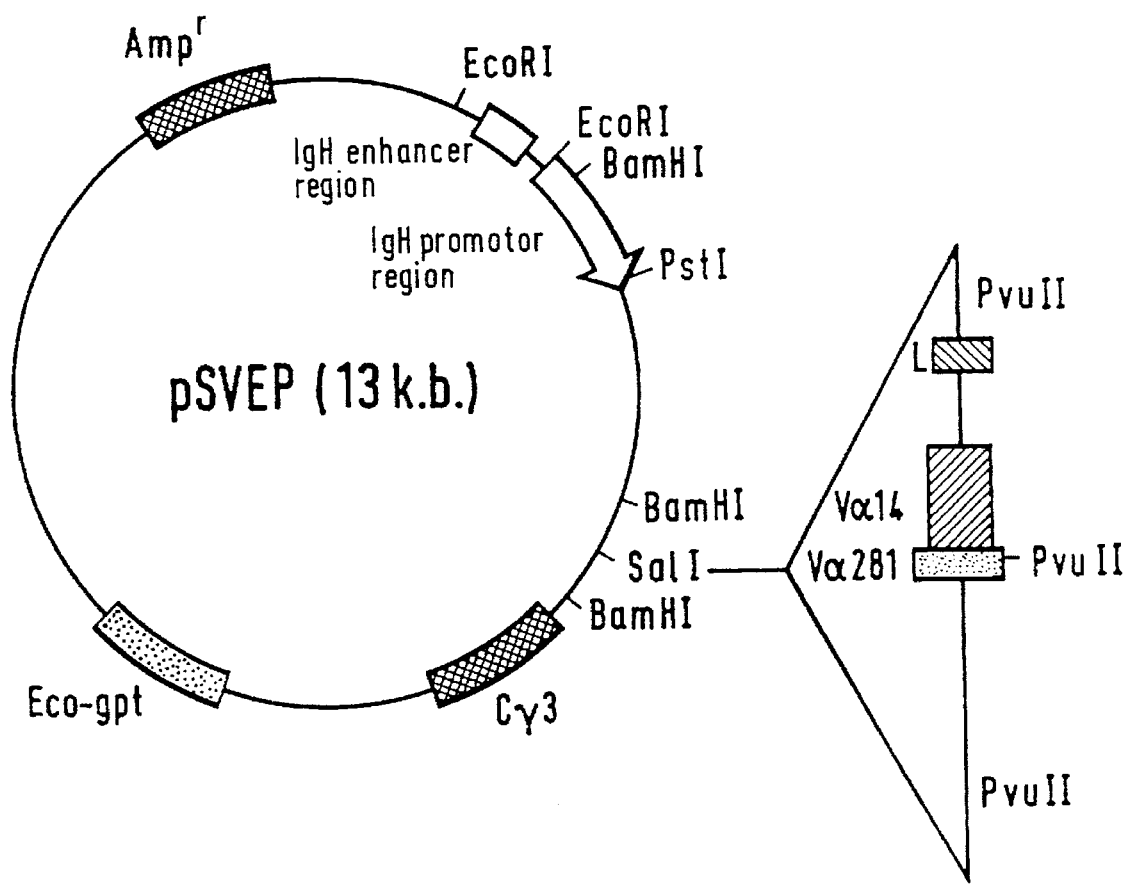
FIG. 2 shows the construction of the expression vector plasmid of the gene encoding the chimeric protein of a T-cell receptor α-chain and an immunoglobulin constant region.

The pSVEP plasmid containing the constant region Cγ3 of mouse IgG was first constructed (Kameyama et al., FEBS Letters, 244, 301 (1989)], into which Vα14Jα281 cDNA was inserted at the Sal I site (See, FIG. 2). The vector (30 μg) was introduced into J558L mouse myeloma cells ($2\times10^6$) by electroporation. The introduced cells were selected in 20% FCS-RPMI 1640 medium containing 20 mg/ml of mycophenolic acid and secretion of Vα14Jα281Cγ3 chimeric protein was confirmed in the supernatant by ELISA. The soluble Vα14Jα281Cγ3 chimeric protein secreted in the supernatants was purified from the culture supernatant by affinity chromatography using protein G.

EXAMPLE 3

Inhibitory effect on antibody production of anti-Vα14 monoclonal antibody

Mice were immunized with Vα14Jα281 and the monoclonal antibody to Vα14 was prepared according to a conventional method.

Figure 3:
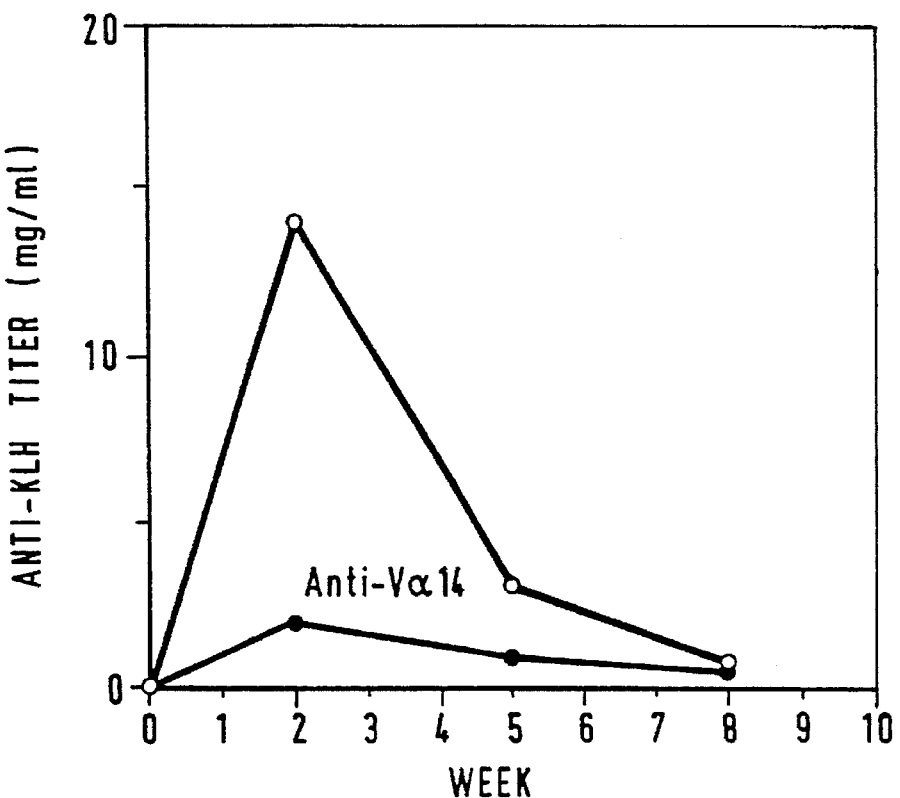
FIG. 3 shows the inhibition of the antibody production to the KLH antigen of the mice pre-treated with the anti-Vα14 monoclonal antibody. In this Figure, the closed circles show the anti-Vα14 monoclonal antibody-administered group, while the open circles show the control group.
Figure 4:
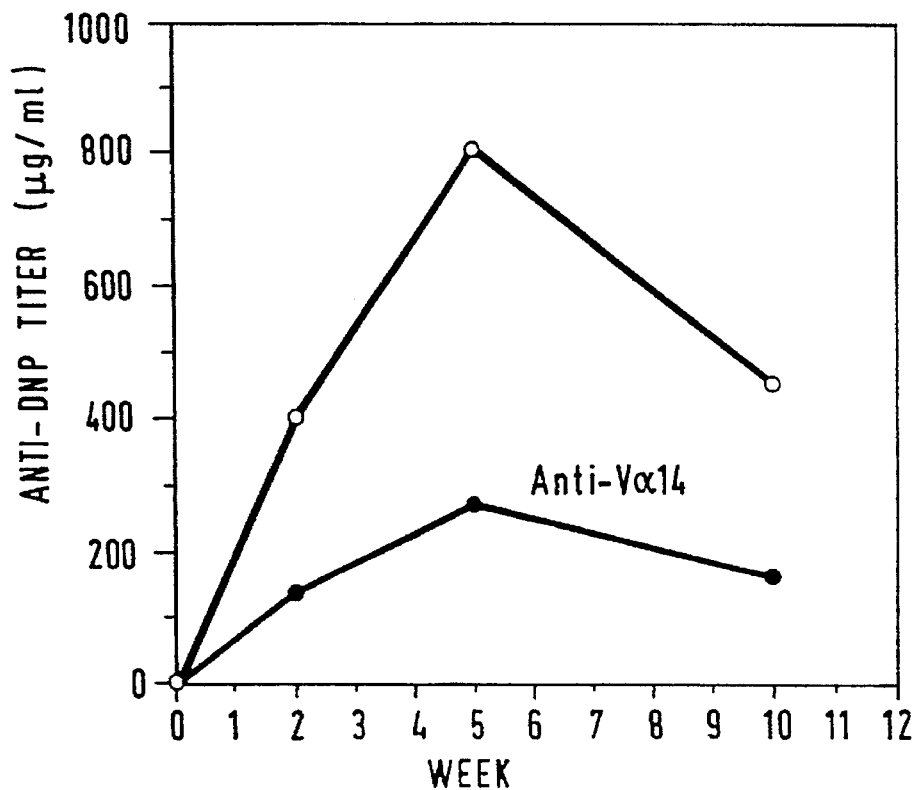
FIG. 4 shows the inhibition of the antibody production to the DNP antigen of the mice pre-treated with the anti-Vα14 monoclonal antibody. In this Figure, the closed circles show the anti-Vα14 monoclonal antibody-administered group, while the open circles show the control group.

The Vα14Jα281 monoclonal antibody (100 μg) was intraperitoneally administered to mice every week starting from two weeks before commencing immunization with DNP-KLH. And further, a mixture of DNP-KLH (100 μg), pertussis vaccine (hereinafter abbreviated as PV: Chiba Serum Institute) and aluminum hydroxide (Wako Pure Chemical Ind., Ltd.) was prepared and mice were immunized at the week 0 as indicated in FIG. 3 and FIG. 4. Administration of the anti-Vα14Jα281 monoclonal antibody to mice was continued up to the 3rd week after the immunization with DNP-KLH. Amounts of the anti-KLH antibody and of the anti-DNP antibody were determined by ELISA.

As apparent from the FIG. 3 and FIG. 4, the antibodies to KLH and DNP were produced well in the control mouse groups not given the anti-Vα14 monoclonal antibody. In the mice given the monoclonal antibody to Vα14, production of both anti-KLH antibody and anti-DNP antibody was inhibited. These results show that the anti-Vα14 monoclonal antibody could stimulate the Ts antigen-non-specifically and promote its immuno-suppression activity.

EXAMPLE 4

Therapeutic effect on IDDM animal model

The IDDM animal model was prepared according to the Bendelac et al. method [Bendelac et al., J. Exp. Med., 166, 823 (1987); Yasunami and Bach, Eur. J. Immunol., 18, 481 (1988); Pankewycz et al., 21, 873 (1991)]. Namely, the NOD mice aged 12 weeks were given cyclophosphamide at a dose of 4 mg. After 2–3 weeks, 50% of the mice showed a positive glycosuria in a test. The $3\times10^7$ lymphocytes out of those separated from the spleen of the mice and were intravenously injected to the NOD mice aged 5 weeks which had been irradiated at 800 rads. The lymphocyte-transplanted mice were found to show a positive glycosuria at a high rate after 2–3 weeks.

In order to administer the Vα14Jα281Cγ3 chimeric protein, 8 female mice were prepared. The mice were divided to 2 groups, one group which consisted of 4 animals and was not administered anything as a negative control, and another group of 4 animals which was administered the Vα14Jα281Cγ3 chimeric protein. Administration was performed by mixing the Vα14Jα281Cγ3 chimeric protein (100 μg) with aluminum gel and injecting intraperitoneally to the NOD mice transplanted with the lymphocytes. Thereafter, the Vα14Jα281Cγ3 chimeric protein only was intraperitoneally administered at a dose of 50 μg twice a week, which was continued in this mode for 3 and a half weeks (a total of 7 times). The onset of IDDM was evaluated by determinating a glucose amount in urine according to a urinoglucose test paper method. The results are shown in Table 1.

50 μg of the Vα14Jα281Cγ3 chimeric protein was administered to mice, one group consisting of 3 animals, while a phosphate buffered saline (PBS) was administered to another group of 3 mice. Administration of the chimeric protein or PBS was made once on the day when transplantation of lymphocytes was conducted.

The results of the experiment wherein the Vα14Jα281Cγ3 chimeric protein was given to mice without mixed aluminum gel are shown in Table 2.

TABLE 2

Effect of the Vα14Jα281Cγ3 chimeric protein without mixed aluminum gel on IDDM onset model mice

| Mouse No. | Treatment | Course after administration (week) | | | | | | | | | | | | |
|---|---|---|---|---|---|---|---|---|---|---|---|---|---|
| | | 0 | 1 | 2 | 3 | 4 | 5 | 6 | 7 | 8 | 9 | 10 | 11 | 12 |
| 1 | Vα14Jα281* | – | – | – | – | – | – | – | – | – | – | – | – | – |
| 2 | Vα14Jα281* | – | – | – | – | – | – | – | – | – | – | – | – | – |
| 3 | Vα14Jα281* | – | – | – | – | – | – | – | – | – | – | – | – | – |
| 1 | PBS** | – | – | –+ | ++ | ++ | ++ | ++ | ++ | ++ | ++ | ++ | ++ | ++ |
| 2 | PBS** | – | – | – | ±± | – | – | ±+ | +± | – | – | – | – | – |
| 3 | PBS** | – | – | – | – | – | – | ±+ | ±– | – | – | – | – | – |

*Group to which 50 μg of the Vα14Jα281Cγ3 chimeric protein were administered.
**Group to which phosphate-buffered saline was administered.

TABLE 1

Effect of the Vα14Jα281Cγ3 administration on IDDM onset model mice

| Mouse No. | Treatment | Course after institution of therapy (week) | | | | | | | | | |
|---|---|---|---|---|---|---|---|---|---|---|---|
| | | 0.5 | 1.0 | 1.5 | 2 | 2.5 | 3 | 3.5 | 4 | 4.5 | 6.5 |
| 1 | Non-treated | – | – | – | – | + | + | + | + | + | + |
| 2 | Non-treated | – | – | – | + | + | + | + | + | + | + |
| 3 | Non-treated | – | – | – | + | + | + | + | + | + | + |
| 4 | Non-treated | – | – | – | + | + | + | + | + | + | + |
| 5 | Vα14Jα281* | – | – | – | – | – | – | – | – | – | – |
| 6 | Vα14Jα281* | – | – | – | – | – | – | – | – | – | – |
| 7 | Vα14Jα281* | – | – | – | – | – | – | – | – | + | + |
| 8 | Vα14Jα281* | – | – | – | – | – | – | – | – | – | – |

*Group to which a mixture of Vα14Jα281Cγ3 chimeric protein and aluminum gel was administered.

In the experiment where a mixture of Vα14Jα281Cγ3 chimeric protein and aluminum gel was administered, three of the four mice not given the Vα14Jα281Cγ3 chimeric protein exhibited their onset at the 2nd week after the lymphocyte transplantation and the remaining one mouse exhibited its onset after 2 and a half weeks. To the contrary, the four mice transplanted with the lymphocytes and given the Vα14Jα281Cγ3 chimeric protein did not exhibit their onset yet up to the 4th week. After one week from discontinuation of the administration of the Vα14Jα281Cγ3 chimeric protein, that is, after 4 and half weeks from the lymphocyte transplantation, one of the mice of the latter group exhibited its onset. Though observed up to the 7th week, these mice were not observed to exhibit any further changes.

Moreover, in order to eliminate influence of aluminum gel, an experiment was conducted wherein the Vα14Jα281Cγ3 chimeric protein only, in the absence of aluminum gel, was given to NOD mice. More specifically, Evaluation was determined by the urine glucose level and "+" indicates that a urine glucose level is 200 mg/dl or more, "–" 200 mg/dl or less and "±" approximately intermediate values between the above two. Three mice given the Vα14Jα281Cγ3 chimeric protein all did not exhibit onset during the observation period of 12 weeks. However, of the PBS-given control 3 mice, one mouse exhibited its onset over the whole period after the second week and two mice exhibited their temporary onset during the said observation period; eventually a slight to severe onset was observed in all PBS-given groups.

As discussed above, the soluble Vα14Jα281 derived from the KLH-specific Ts hybridoma was found to prevent the NOD mice from their onset of diabetes as TsF in an antigen-non-specific manner.

The suppressor T-cell receptor α-chain illustrated by this invention may be useful as a prophylactic and therapeutic agent against autoimmune diseases generated to a wide variety of autoantigens exhibiting a different specificity of the suppressor T-cells.

What is claimed is:

1. A prophylactic and therapeutic method for the treatment of autoimmune induced insulin dependent diabetes mellitus which comprises administering a prophylactically or therapeutically effective amount of a chimeric protein containing Vα14Jα281, which chimeric protein is formed by fusing the soluble T-cell receptor α-chain Vα14Jα281 produced by a suppressor T-cell to a constant region of immunoglobulin G, to a subject in need of such treatment.

2. The prophylactic and therapeutic method as claimed in claim 1, wherein said chimeric protein contains Vα14Jα281Cγ3.

* * * * *